United States Patent
Aschbacher et al.

(10) Patent No.: US 8,019,429 B2
(45) Date of Patent: Sep. 13, 2011

(54) CARRIER AND ENVELOPE TRIGGERED COCHLEAR STIMULATION

(75) Inventors: Ernst Aschbacher, Innsbruck (AT); Peter Schleich, Vill (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 12/729,701

(22) Filed: Mar. 23, 2010

(65) Prior Publication Data
US 2010/0249880 A1    Sep. 30, 2010

Related U.S. Application Data

(60) Provisional application No. 61/162,760, filed on Mar. 24, 2009.

(51) Int. Cl.
*A61N 1/36* (2006.01)

(52) U.S. Cl. ............... 607/56; 607/55; 607/57; 607/136; 607/137; 600/379

(58) Field of Classification Search ............... 607/55–57, 607/136–137; 600/379
See application file for complete search history.

(56) References Cited

U.S. PATENT DOCUMENTS

| | | | | |
|---|---|---|---|---|
| 4,284,856 | A | 8/1981 | Hochmair et al. | 179/107 |
| 4,428,377 | A | 1/1984 | Zollner et al. | 128/419 R |
| 4,515,158 | A | 5/1985 | Patrick et al. | 128/419 R |
| 5,215,085 | A | 6/1993 | von Wallenberg-Pachaly | 128/420.6 |
| 5,434,924 | A | 7/1995 | Jampolsky | 381/68.4 |
| 5,601,617 | A | 2/1997 | Loeb et al. | 607/56 |
| 5,749,912 | A | 5/1998 | Zhang et al. | 607/57 |
| 5,938,691 | A | 8/1999 | Schulman et al. | 607/57 |
| 6,175,767 | B1 | 1/2001 | Doyle, Sr. | 607/57 |
| 6,219,580 | B1 | 4/2001 | Faltys et al. | 607/57 |
| 6,289,247 | B1 | 9/2001 | Faltys et al. | 607/57 |
| 6,295,472 | B1 | 9/2001 | Rubinstein et al. | 607/55 |
| 6,594,525 | B1 | 7/2003 | Zierhofer | 607/57 |
| 6,600,955 | B1 | 7/2003 | Zierhofer | 607/57 |

(Continued)

FOREIGN PATENT DOCUMENTS

EP   1338301   8/2003

(Continued)

OTHER PUBLICATIONS

McKay, "The effect of rate of stimulation on perception of spectral shape by cochlear implantees," J. Acoust. Soc. Am., vol. 118, No. 1, pp. 386-392, 2005.

(Continued)

*Primary Examiner* — Carl H Layno
*Assistant Examiner* — Natasha N Patel
(74) *Attorney, Agent, or Firm* — Sunstein Kann Murphy & Timbers LLP

(57) ABSTRACT

Generation of electrode stimulation signals for an implanted electrode array is described. An acoustic audio signal is processed to generate band pass signals which include a fine structure carrier signal and a modulator envelope signal. For each band pass signal, fine time structure information is extracted from the carrier signal to determine a sequence of stimulation event signals. For one or more low frequency band pass signals, the modulator envelope signal is sampled synchronously with the carrier signal to create envelope weighted stimulation event signals. For one or more higher frequency band pass signals, if and only if the modulator envelope signal exceeds a sampling threshold value, then the modulator envelope signal is sampled synchronously with the carrier signal to create envelope weighted stimulation event signals. The envelope weighted stimulation event signals are then processed to produce electrode stimulation signals for the implanted electrode array.

25 Claims, 7 Drawing Sheets

U.S. PATENT DOCUMENTS

| | | |
|---|---|---|
| 6,778,858 B1 | 8/2004 | Peeters .......................... 607/57 |
| 6,826,430 B2 | 11/2004 | Faltys et al. ................. 607/137 |
| 7,149,583 B1 | 12/2006 | Litvak ............................ 607/57 |
| 2001/0031909 A1 | 10/2001 | Faltys et al. ..................... 600/25 |
| 2004/0082985 A1 | 4/2004 | Faltys et al. ................... 607/116 |
| 2005/0107843 A1 | 5/2005 | McDermott et al. ............ 607/57 |
| 2005/0203589 A1 | 9/2005 | Zierhofer ........................ 607/57 |
| 2006/0052841 A1 | 3/2006 | Daly et al. ....................... 607/57 |
| 2006/0080087 A1 | 4/2006 | Vandali et al. ................ 704/207 |
| 2006/0100672 A1 | 5/2006 | Litvak ............................ 607/57 |
| 2006/0227986 A1 | 10/2006 | Swanson et al. ............. 381/312 |
| 2006/0265061 A1 | 11/2006 | Kwon et al. ..................... 623/10 |
| 2007/0156202 A1 | 7/2007 | Zierhofer ........................ 607/57 |
| 2007/0225776 A1 | 9/2007 | Fritsch et al. .................. 607/57 |
| 2010/0198300 A1 | 8/2010 | Smith ............................. 607/57 |

FOREIGN PATENT DOCUMENTS

| | | |
|---|---|---|
| WO | WO 99/35882 | 7/1999 |
| WO | WO 9949815 | 10/1999 |
| WO | WO 0103622 | 1/2001 |
| WO | WO 0113991 | 3/2001 |
| WO | WO 0119135 | 3/2001 |
| WO | WO 0119304 | 3/2001 |
| WO | WO 02096153 | 11/2002 |
| WO | WO 2005113064 | 12/2005 |
| WO | WO 2006119069 | 11/2006 |

OTHER PUBLICATIONS

Secker-Walker, et al. "*Time-domain analysis of auditory-nerve-fiber firing rates,*" J. Acoust. Soc. Am., vol. 88, No. 3, pp. 1427-1436, 1990.

Zeng, et al. "*Cochlear Implants: System Design, Integration, and Evaluation,*" IEEE Reviews in BioMed. Eng., vol. 1, pp. 115-142, 2008.

European Patent Office; Authorized Officer: Pereda, D., International Search Report and Written Opinion, International Application No. PCT/US2008/079923, mailed Jan. 27, 2009, 14 pages.

European Patent Office; Authorized Officer: Aronsson, F., International Search Report and Written Opinion, International Application No. PCT/IB2005/002349, mailed Nov. 16, 2005, 13 pages.

European Patent Office; Authorized Officer: Smit, J., International Search Report and Written Opinion, International Application No. PCT/IB2009/005813, mailed Sep. 3, 2009, 15 pages.

European Patent Office; Authorized Officer: Edward, V., Notification of Transmittal of the International Search Report and The Written Opinion of the International Searching Authority, or the Declaration, International Application No. PCT/US2010/028276, mailed Sep. 6, 2010, 6 pages.

European Patent Office; Authorized Officer: Edward, V., Written Opinion of the International Searching Authority, International Application No. PCT/US2010/028276, mailed Sep. 6, 2010, 5 pages.

Kral, A., et al, "Spatial resolution of cochlear implants: the electrical field and excitation of auditory afferents", *Hearing Research*, vol. 121 (1998, pp. 11-28.

Loizou, P.C., "Signal Processing for Cochlear Prosthesis: A Tutorial Review", *IEEE*, Jan. 1997, pp. 881-885; 0-7803-3694-1/97.

Loizou, P.C., "Signal-Processing Techniques for Cochlear Implants", *IEEE Engineering in Medicine and Biology*, May/Jun. 1999, pp. 34-46.

Wilson, B.S., et al, "Comparative Studies of Speech Processing Strategies for Cochlear Implants", *Laryngoscope*, vol. 96, No. 10, pp. 1068-1077, Oct. 1988.

Wilson, B. S., et al, "Better speech recognition with cochlear implants", *Nature*, vol. 352, pp. 236-238, Jul. 18, 1991.

Wilson, B. S., et al, "Seventh Quarterly Progress Report; Speech Processors for Auditory Prostheses", *Center for Auditory Prosthesis Research*, pp. 1-69, 1994.

Wilson, B. S., et al, "Temporal Representations With Cochlear Implants", *The American Journal of Otology*, 18:530-534, 1997.

Ziese, M., et al, "Speech Understanding with the CIS and the n-of-m Strategy in the MED-EL COMBI 40+ System", *ORL*, 2000;62:321-329.

CARRIER AND ENVELOPE TRIGGERED COCHLEAR STIMULATION

This application claims priority from U.S. Provisional Patent Application 61/162,760, filed Mar. 24, 2009, which is incorporated herein by reference.

FIELD OF THE INVENTION

The present invention relates to medical implants, and more specifically to production of electrode stimulation signals in cochlear implant systems.

BACKGROUND ART

FIG. 1 shows functional signal processing blocks in a typical cochlear implant system where K-Channel Filter Bank 101 pre-processes an initial acoustic audio signal x[n], for example, applying automatic gain control, noise reduction, etc. Each band pass filter in the K-Channel Filter Bank 101 is associated with a specific band of audio frequencies so that the acoustic audio signal x[n] is filtered into some K band pass signals, $x_1[n]$ to $x_K[n]$ where each signal corresponds to the band of frequencies for one of the band pass filters. For example, the initial acoustic audio signal x[n] may be spectrally decomposed into 12 time-domain band pass signals.

The band pass signals, $x_1[n]$ to $x_K[n]$ then are input to a Channel Processor 102 that extracts component signals that reflect specific stimulation information—e.g., a carrier signal containing fine time structure information and a modulator envelope signal. For example, in one specific system, the modulator envelope signal may be calculated using the Hilbert-Transform (incoherent decomposition). Based on these band pass signal signals, the Channel Processor 102 creates for each band pass channel a sequence of envelope weighted stimulation event signals $p_1[n]$ to $p_K[n]$, which represent specific requested stimulation events. For example, a sequence of envelope weighted stimulation event signals $p_1[n]$ to $p_K[n]$ may be based on channel specific sampling sequences (CSSS) as described in U.S. Pat. No. 6,594,525, which is incorporated herein by reference.

Pulse Weighting Module 103 further weights each requested envelope weighted stimulation event signal $p_1[n]$ to $p_K[n]$ based on a weighted matrix of stimulation amplitudes that reflect patient-specific perceptual characteristics to produce a set of channel stimulation signals $q_1[n]$ to $q_L[n]$ that provide an optimal tonotopic electrical representation of the acoustic signal. Equation 1 shows a typical weighting matrix of size M×N:

$$W = \begin{pmatrix} 1 & 0.923 & 0.846 & \ldots & \ldots & 0 & 0 & 0 \\ 0 & 0.077 & 0.154 & \ldots & \ldots & 0 & 0 & 0 \\ 0 & 0 & 0 & \ldots & \ldots & 0 & 0 & 0 \\ \ldots & \ldots & \ldots & \ldots & \ldots & \ldots & \ldots & \ldots \\ 0 & 0 & 0 & \ldots & \ldots & 0.154 & 0.077 & 0 \\ 0 & 0 & 0 & \ldots & \ldots & 0.846 & 0.923 & 1 \end{pmatrix} \quad \text{Equation 1}$$

Matrix weighting of the stimulation pulses is described further in U.S. patent application 61/046,832, filed Apr. 22, 2008, which is incorporated herein by reference. In some embodiments, the number of filter bank channels may be greater than the number of electrode channels (e.g., 128:12). In such an arrangement, the stimulation event signals may be pooled into a smaller number of overlapping macro bands, and within each macro band the channel with the highest envelope is selected for a given sampling interval, as described for example in U.S. patent application 61/145,805, filed Jan. 20, 2009, which is incorporated herein by reference.

Finally, patient-specific fit of the stimulation signals can be further optimized by individual amplitude mapping and pulse shape definition in Pulse Shaper 104 which develops the set of electrode stimulation signals $q_1[n]$ to $q_L[n]$ into a set of output electrode pulses $e_1[n]$ to $e_L[n]$ to the stimulation electrodes in the implanted electrode array to stimulate the adjacent target nerve tissue. For example, this may involve maplaw, scaling, and/or pulse shaping functions.

The most apical region of the cochlea is associated with low-frequency perception. In this region, the corresponding electrode stimulation patterns in existing cochlear implant systems typically use both the fine time structure information of the carrier signal and the modulator envelope signal of the band pass signals to determine the electrode stimulation pattern. The modulator envelope signal defines the stimulation intensity (current, charge), and the fine time structure information determines the time instant when the stimulation occurs. The additional fine time structure information in the carrier signal may be used by the nervous structures in the inner ear, for example, to track changes in fundamental frequency ($F_0$). This may be useful for better speech understanding, better perception of tonal languages and prosodic features, and better perception of music. For example, Channel Specific Sampling Sequences (CSSS) may be generated whenever a zero-crossing of the band pass carrier signal is detected, and the CSSS are weighted by the modulator envelope signal so as to provide both modulator information and fine time structure information. Envelope sampling is not performed on a regular time-grid, but rather is irregular and synchronous to the carrier signal.

The middle and basal regions of the cochlea are associated with the perception of mid- to high frequency audio. In these regions, the modulator envelope signal of the time-domain band pass signals is sampled on a regular time-grid that is independent of the carrier signal. The amount of neural stimulation (current, charge) is, as in the low-frequency region, determined by the amplitude of the modulator envelope signal.

The sampling of the band pass signal modulator envelope signals is thus irregular and carrier synchronous in the low-frequency stimulation channels, and regular and carrier asynchronous in the mid- to high-frequency stimulation channels. So the nervous structures of the inner ear receive these two different types of stimulation patterns.

An algorithm for generating an irregular continuous interleaved stimulation pattern is described in Sit et al., *A Low-Power Asynchronous Interleaved Sampling Algorithm For Cochlear Implants That Encodes Envelope And Phase Information*, IEEE Trans. Biomed. Eng., vol. 54, no. 1, pp. 138-149, January 2007; incorporated herein by reference. The described algorithm includes the following steps:

1) The system receives as inputs half-wave rectified currents from a bank of band pass analysis filters. These could be actual currents such as those generated by an analog processor, or a digital version as produced by a digital signal processor.
2) Each stimulation channel is associated with an integrate-and-fire neuron that receives the current input from that channel to charge up its neuronal capacitance from the ground state. This begins what is referred to as a "race-to-spike."
3) The first neuron to reach a fixed voltage threshold "wins" and resets all capacitors back to zero. This ensures that the interleaved stimulation requirement is satisfied, since there can be only one winner.

4) The winning neuron then fires a current spike (which is an asynchronous timing event) on its electrode that is scaled by the channel envelope energy.

5) Once a neuron wins, its input current is inhibited (i.e., weakened) for a period determined by a relaxation time constant, to prevent it from winning repeatedly.

6) After the winning neuron has fired its spike, the neuronal "race-to-spike" (Step 2) is started again.

In U.S. Pat. No. 7,310,558, another electrode stimulation strategy is presented which produces irregular stimulation on all channels. The algorithm describes:

1) Processing a received audio signal to define signals in a set of frequency channels, 2) Determining a time and intensity for each of one or more peaks in each of the frequency signals, 3) Prioritizing each of the peaks according to a predetermined instruction set, 4) Specifying a minimum time interval between the peaks of each of the frequency signals, 5) Discarding peaks occurring within a minimum time interval, 6) Placing non-discarded peaks, in order of priority, into time slots of a buffer corresponding to the times the non-discarded peaks occur in the signals, and 7) Outputting from the buffer a set of data for use in generating stimulus instructions.

SUMMARY OF THE INVENTION

Generation of electrode stimulation signals for an implanted electrode array is described. An acoustic audio signal is processed to generate band pass signals which include a fine structure carrier signal and a modulator envelope signal. For each band pass signal, fine time structure information is extracted from the carrier signal to determine a sequence of stimulation event signals. For one or more low frequency band pass signals, the modulator envelope signal is sampled synchronously with the carrier signal to create envelope weighted stimulation event signals. For one or more higher frequency band pass signals, if and only if the modulator envelope signal exceeds a sampling threshold value, then the modulator envelope signal is sampled synchronously with the carrier signal to create envelope weighted stimulation event signals. The envelope weighted stimulation event signals are then processed to produce electrode stimulation signals for the implanted electrode array.

Processing the envelope weighted stimulation event signals may include one or more of mapping the envelope weighted stimulation event signals to a set of electrode stimulation channels for producing the electrode stimulation signals, optimizing the envelope weighted stimulation signals for perception by the individual patient, and/or developing a desired pulse shape (e.g. biphasic pulse) for the electrode stimulation signals.

Extracting fine time structure information may be based on zero crossings of the band pass signals. For each band pass signal, the envelope weighted stimulation signals may be suppressed if one or more physiological state considerations occur such as a refractory state of target nervous tissue and/or adjacent channel stimulation activity. In some embodiments, the sampling threshold value may be a function of channel signal quality, one or more physiological criteria, and/or one or more temporal characteristics of the modulator envelope signal.

Embodiments of the present invention also include a computer program product implemented in a computer readable storage medium for generating electrode stimulation signals for an implanted electrode array according to any of the above. Embodiments also include a cochlear implant system operating according to any of the above.

DETAILED DESCRIPTION OF SPECIFIC EMBODIMENTS

Embodiments of the present invention extend the concept of irregular carrier synchronous sampling of the modulator envelope signal to include the mid- to high frequency stimulation channels. The resulting stimulation pattern is synchronous to the carrier signals in the respective band pass signals, but can avoid an overly high stimulation rate by also factoring in temporal characteristics of the modulator envelope signal and physiological criteria such as nerve refractory states and/or masking effects. This approach retains the connection between the carrier signal and the modulator envelope signal in deriving the electrode stimulation signals. The temporal characteristics of the modulator envelope signal also are explicitly taken into account, which may result in more accurate perception of time structure information (e.g., inter-aural time-differences) and amplitude structure information (e.g., speech features) of the modulator envelope signal.

Figure 1:
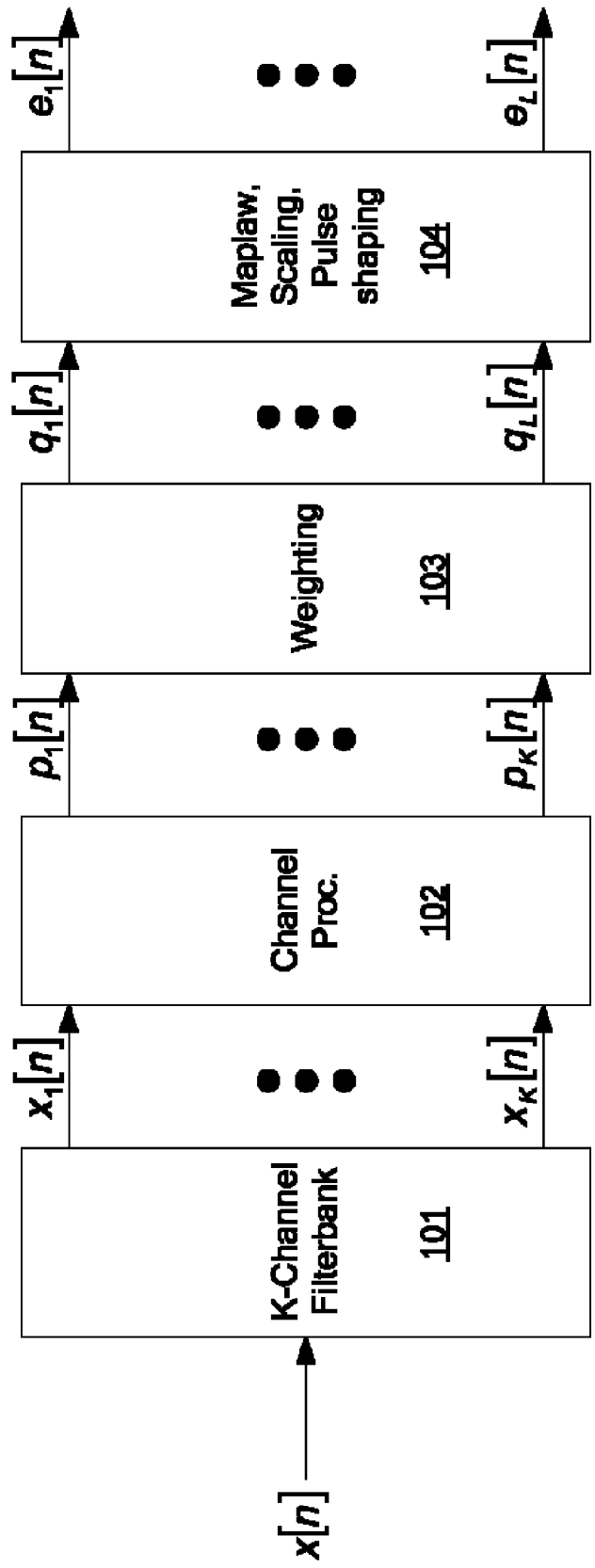
FIG. 1 shows functional signal processing blocks in a typical cochlear implant system.
Figure 2:
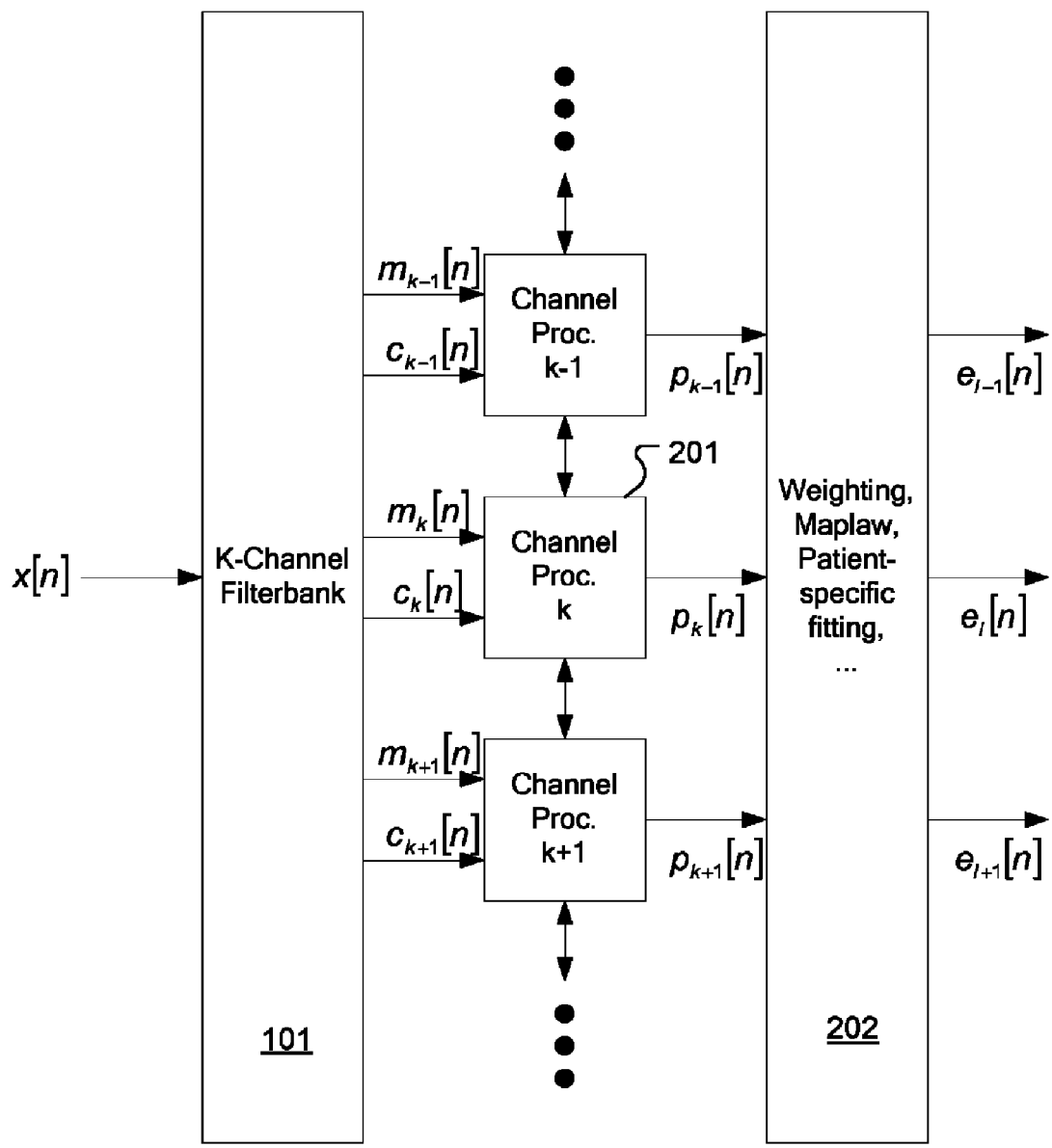
FIG. 2 shows further detail with regards to the signal processing blocks in a typical embodiment of a cochlear implant system.

FIG. 2 shows further detail with regards to the signal processing blocks in a cochlear implant system according to one exemplary embodiment. An input acoustic audio signal $x[n]$ is processed by K-Channel Filter Bank 101 to generate K time domain band pass signals, each of which includes a fine structure carrier signal $c_k[n]$ and a modulator envelope signal $m_k[n]$. In some embodiments, the number of band pass channels may equal the number of electrode stimulation channels, while in other embodiments, there may be significantly more band pass filter channels than electrode stimulation channels. For example, one embodiment may have 128 band pass filter channels and 12 electrode stimulation channels.

From each band pass signal, an associated Channel Processor 201 extracts fine structure time information from the carrier signal $c_k[n]$ to determine a sequence of stimulation event signals which are weighted by the modulator envelope signal $m_k[n]$ to form sequences of envelope weighted stimulation event signals $p_k[n]$. More specifically, for one or more low frequency band pass signals, the envelope signal $m_k[n]$ is sampled synchronously with the carrier signal $c_k[n]$ to create the envelope weighted stimulation event signals $p_k[n]$. Also, for one or more higher frequency band pass signals—if and only if the envelope signal $m_k[n]$ exceeds a sampling threshold value $s_T$—then the envelope signal $m_k[n]$ is sampled synchronously with the carrier signal $c_k[n]$ to create envelope weighted stimulation event signals $p_k[n]$. The envelope weighted stimulation event signals $p_k[n]$ are then processed to produce electrode stimulation signals $e_L[n]$ for the implanted electrode array.

In the low frequency channels (e.g., the first four or so stimulation channels), envelope weighted stimulation event signals $p_k[n]$ (e.g., CSSS signals) may be generated with each zero-crossing of the carrier signal $c_k[n]$. Since the bandwidth of the low frequency band pass channels is typically relatively small, the envelope signal $m_k[n]$ varies rather slowly over time. Thus, a relatively low sampling rate based on the corresponding carrier signal $c_k[n]$ is adequate to detect and transmit features of the envelope signal $m_k[n]$. Since the bandwidth of mid- to high-frequency stimulation channels is relatively large compared to the low-frequency channels, the envelope signal $m_k[n]$ varies faster than for low-frequency stimulation channels.

Figure 3:
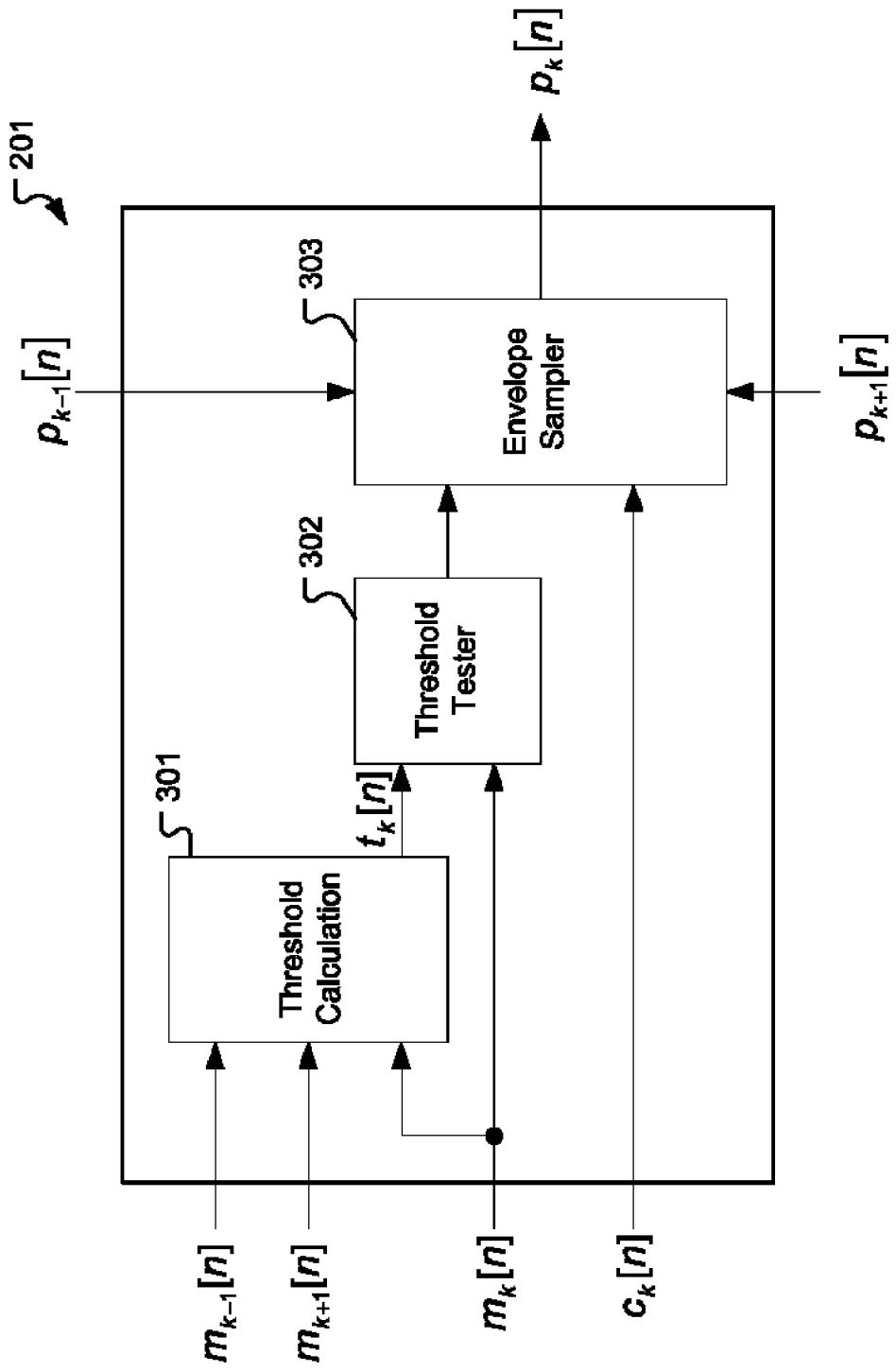
FIG. 3 shows further functional detail of the signal processing in the k-th band pass channel.
Figure 4:
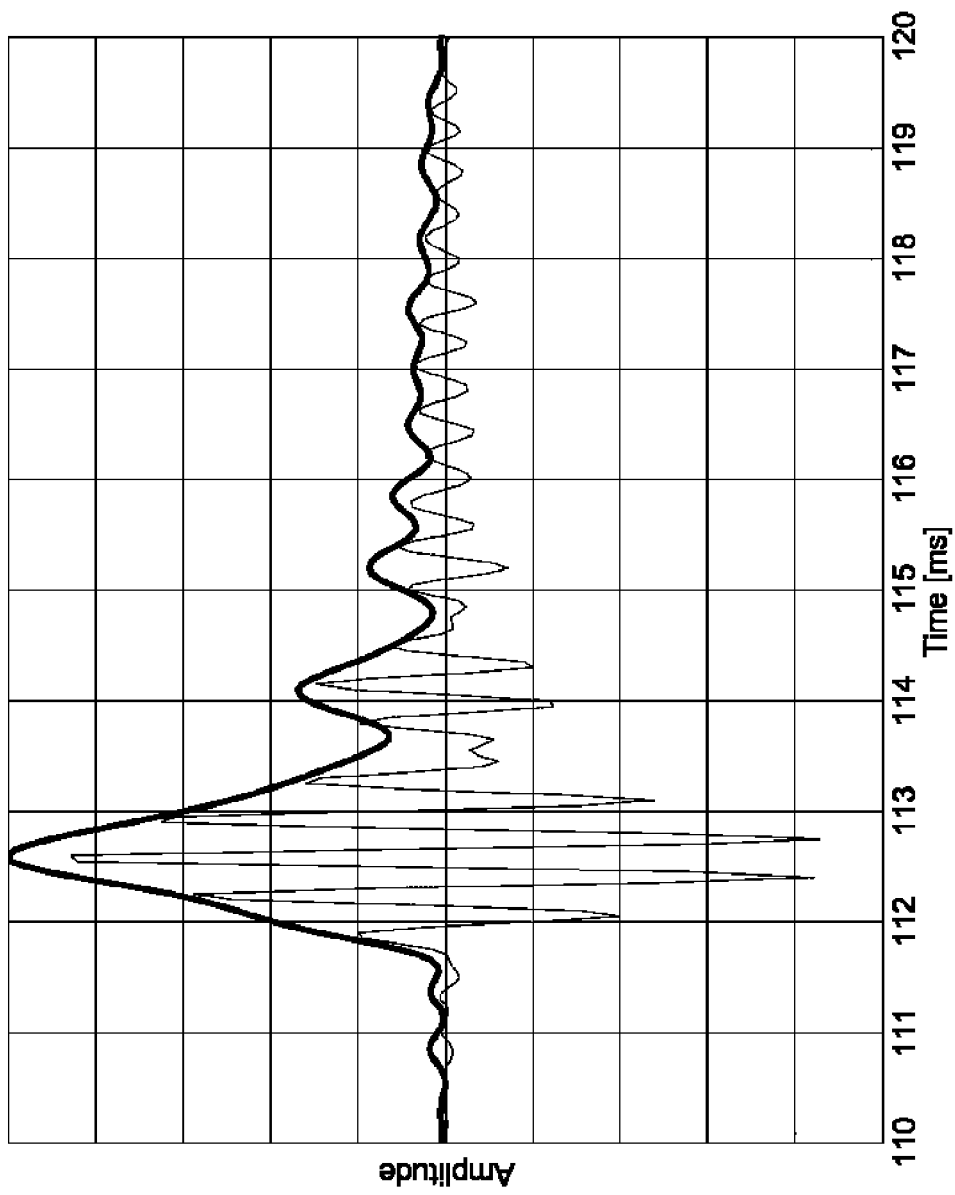
FIG. 4 shows an example of a band pass signal showing the carrier signal (thin curve) and the modulator envelope signal (thick curve).

For example, FIG. 3 shows various functional blocks of the Channel Processor 201 for the $k^{th}$ mid- to high-frequency channel according to one specific embodiment. FIG. 4 shows an example of a typical band pass signal for a mid- to high-frequency stimulation channel having a carrier signal $c_k[n]$ (thin line) and an envelope signal $m_k[n]$ (thick line). Threshold Calculation Module 301 determines a sampling threshold value $s_T$ based on the $k^{th}$ envelope signal $m_k[n]$. Threshold Calculation Module 301 may consider one or more physiological criteria to address neuronal adaptation effects, masking effects, or other physiological effects. For example, in FIG. 3, the Threshold Calculation Module 301 receives the envelope signals $m_{k-1}[n]$ and $m_{k+1}[n]$ of the directly neighboring channels as additional inputs to account for a masking effect from the neighboring channels.

Threshold Calculation Module 301 may also take into account other factors such as signal quality. For example, this may be based on the actual or estimated "long-time" signal-to-noise ratio (SNR) in the stimulation channel such that for a poor SNR, the value of the sampling threshold value $s_T$ increases to permit stimulation only where the envelope signal $m_k[n]$ is large and, therefore, the instantaneous SNR is relatively good. Similarly, stimulation is avoided when the envelope signal $m_k[n]$ has a low level such that the SNR is relatively poor. Stimulation channels with a high or reasonable SNR can be stimulated and are not blocked by channels with a poor SNR.

Figure 5:
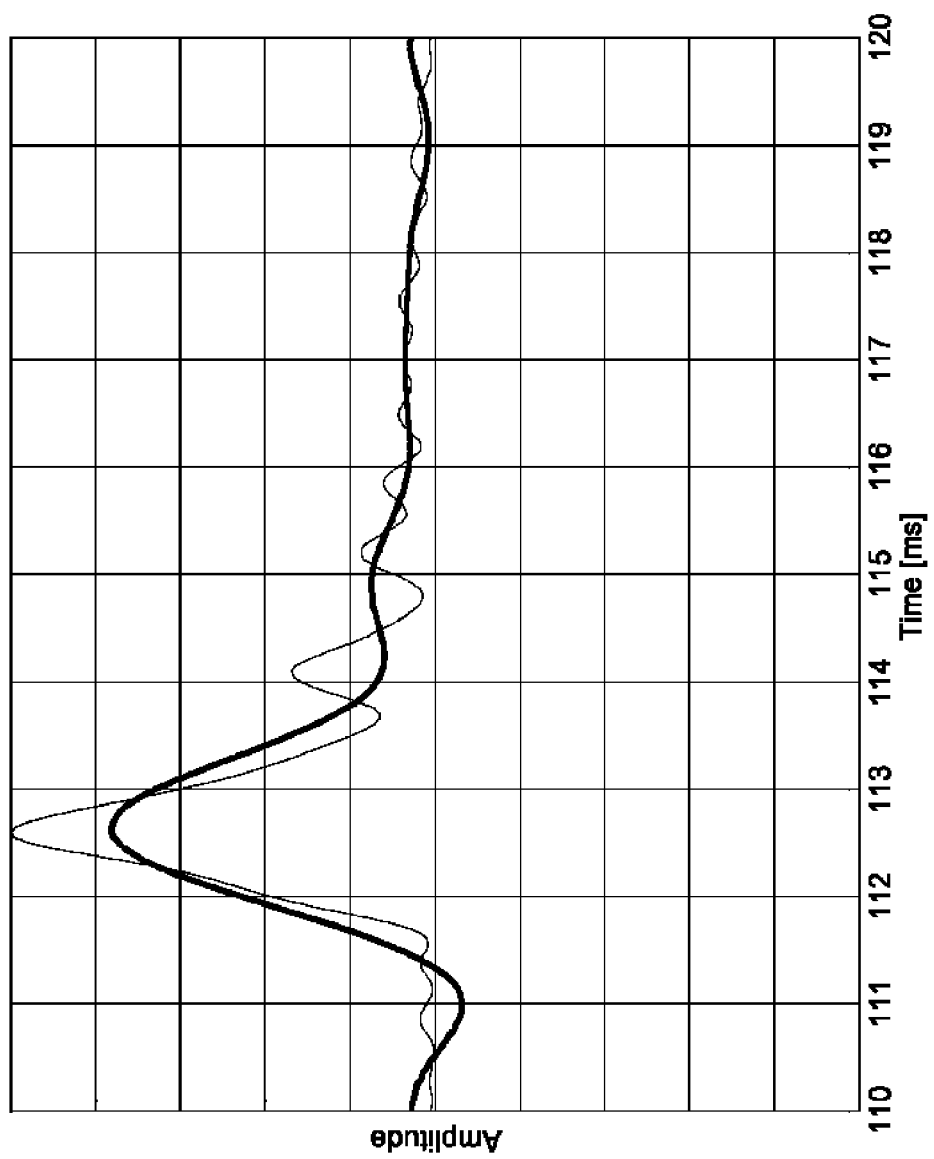
FIG. 5 shows an example of a modulator envelope signal (thin curve) and a sampling threshold signal (thick curve).

In FIG. 3, Threshold Tester Module 302 determines if the envelope signal $m_k[n]$ is above or below the sampling threshold value. FIG. 5 shows an example of the envelope signal $m_k[n]$ (thin line) in comparison to a corresponding sampling threshold value signal (thick line). When enabled by the Threshold Tester Module 302, Envelope Sampler Module 303 processes the carrier signal $c_k[n]$ to determine a time grid for when the envelope signal $m_k[n]$ is sampled. For example, Envelope Sampler Module 303 may use the time instants of the zero-crossings (e.g., from positive to negative) of the carrier signal $c_k[n]$ to determine the sampling time-grid. When the envelope signal $m_k[n]$ is above the sampling threshold value and a zero-crossing of the carrier signal $c_k[n]$ occurs, then Envelope Sampler Module 303 samples the envelope signal $m_k[n]$ to produce the envelope weighted stimulation event signal $p_k[n]$. This in effect represents to a reduction in the sampling rate since sampling does not occur when the envelope signal $m_k[n]$ is below the sampling threshold value.

Figure 6:
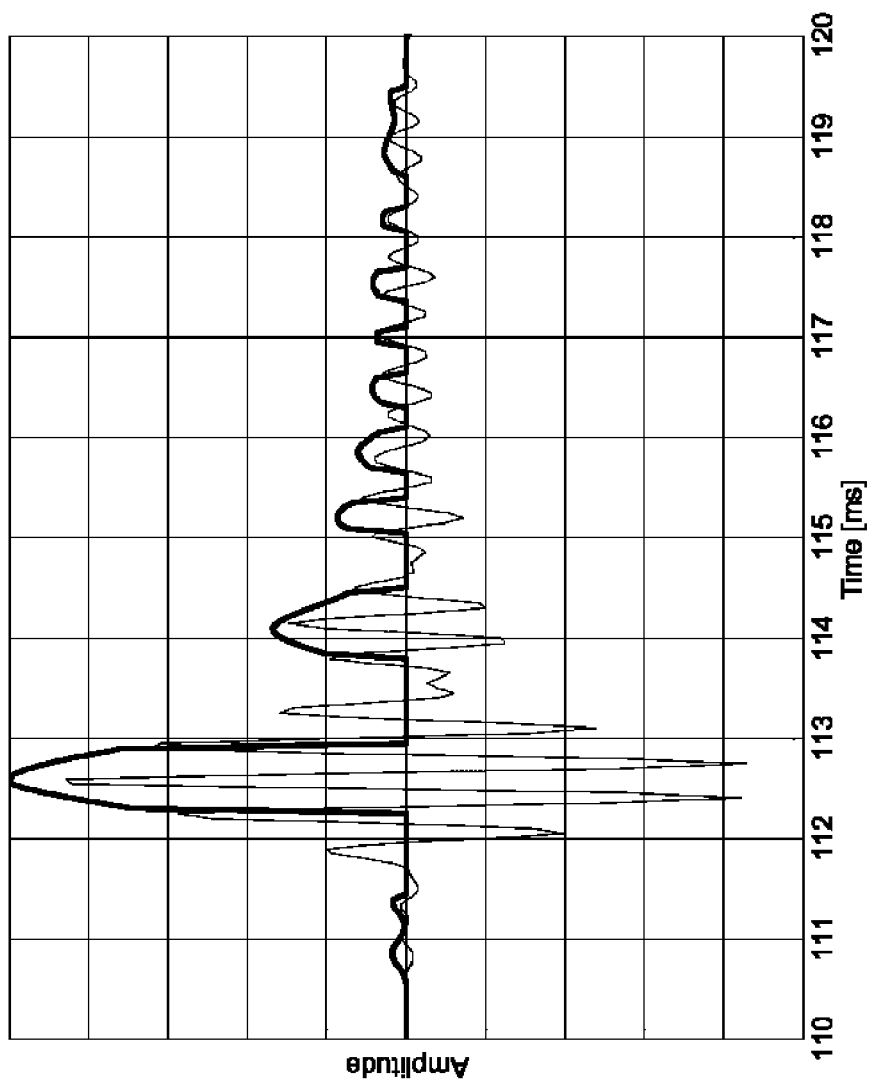
FIG. 6 shows an example of a band pass carrier signal (thin curve) and a supra-threshold (gated) modulator envelope signal (thick curve).
Figure 7:
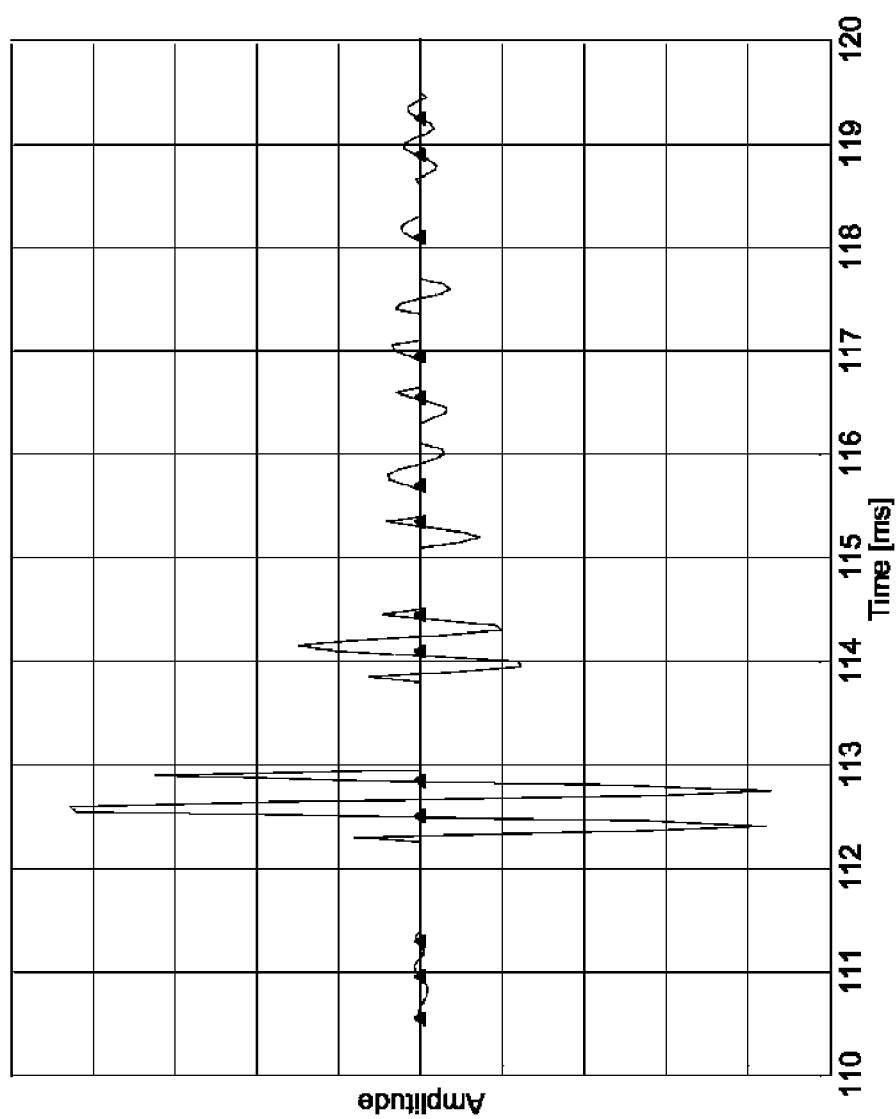
FIG. 7 shows an example of a gated band pass signal (thin curve) and stimulation time-points (triangle markers).

For lower frequency band pass signals, the sampling rate is relatively low (hundreds of Hertz) and correspondingly, the sampling time-grid covers some milliseconds. For the mid- to high-frequency band pass signals, the sampling rate is relatively higher (up to the maximum delivered audio frequency, e.g., 8.5 kHz), and therefore, on a finer sampling time-grid of some tenths of milliseconds. The time resolution thus increases from low to high frequency band pass channels. FIG. 6 shows an example of the corresponding supra-threshold gated envelope signal (thick line) with regards to the carrier signal (thin line). FIG. 7 shows an example for one mid- to high-frequency stimulation channel of the envelope weighted stimulation event signal $p_k[n]$ that is produced, where the stimulation time-points are shown by the triangular markers. Since, as in the low-frequency stimulation channels, the envelope sampling is still synchronous with the carrier signal, the fine-time structure is still present in the stimulation sequence and the stimulation amplitude is determined by the value of the modulator envelope signal $m_k[n]$ at the stimulation time-points.

The Envelope Sampler Module 303 may further condition generation of the envelope weighted stimulation event signals $p_k[n]$ on there being a high probability that a nervous event will occur in response—i.e., the targeted nervous structure is ready to "fire." In other words, the stimulation rate may be decreased or controlled to a physiologically meaningful level. For example, the Envelope Sampler Module 303 may take into account whether or not the target nervous structure is in a refractory state from a preceding stimulation event. In addition or alternatively, the effects of neighboring channels also may be taken into account. In FIG. 3, Envelope Sampler Module 303 processes the envelope weighted stimulation event signals $p_{k+1}[n]$ and $p_{k-1}[n]$ of the adjacent stimulation channels to correct for lateral masking where the current field spread acts to partially stimulate the nervous population of an adjacent channel. Then if a neighboring channel has just released a stimulation pulse so that some of the nervous structure is in a refractory state and temporarily cannot be excited, the Envelope Sampler Module 303 can suppress or adjust the amplitude of the envelope weighted stimulation event signal $p_k[n]$ so that the current need is minimized.

The transition between a purely carrier synchronous sampling and stimulation (as in lower frequency channels) to combined carrier synchronous and envelope triggered (gated) sampling and stimulation (as in higher frequency channels) can be adjustable; e.g., the transition can be moved from band four to band six, or from band four to band one. The resulting envelope weighted stimulation event signals $p_k[n]$ is homogeneous in the sense that over the entire processed frequency range, the stimulation is irregular but coupled to the band pass signal. This is in contrast to existing arrangements (such as FSP coding) with a strict division into regions with irregular stimulation and regions with regular stimulation.

Embodiments such as those described above offer greater modulation depth than with prior art approaches. Such irregular sampling provides a better representation of envelope patterns ("signal-events") in higher frequency channels than the conventional regular sampling with a fixed sampling grid, since the modulation depth of the stimulation is increased. Stimulation occurs when something is happening in the band pass signal.

There is also improved temporal accuracy. The envelope patterns are detected with a high temporal accuracy since the fast (but irregular) sampling frequency is derived from the zero-crossings of the carrier signal in higher frequency channels (up to 7-8 kHz), which is significantly greater than with a fixed sampling frequency of, e.g., 1.5 kHz. Such a high accuracy may be advantageous in bilateral implanted users since the interaural time differences (ITDs) of envelope patterns between the ears are more accurately represented in time. The sampling of the envelope signal is in some sense associated with or triggered by the modulator envelope itself.

A further advantage may be reflected in a reduction of the stimulation rate that in turn leads to a reduction of consumed battery power. This is due to the fact that stimulation pulses are generated only if signal events are detected in the envelope signal (i.e., the envelope signal is above the sampling threshold), the nerves are prepared to be stimulated (i.e., not in a refractory state), and the signal quality is acceptable.

In the prior art approach described by Sit et al., carrier information is not explicitly considered, although it is clamed that the stimulation pulses are still correlated up to a certain amount (which is not quantified) with the phase of the band pass signals (Sec. III, p. 140). Furthermore, in Sit et al. all the stimulation channels, regardless of the frequency region, are processed in the same way, and there is no special consideration of the modulator envelope signal as described above.

The algorithm described in U.S. Pat. No. 7,310,558 does not consider the modulator envelope signal and the carrier signal separately. Signal peaks are selected, whereas in the embodiments described above, the stimulation pattern reflects the modulator envelope signal with a high time accuracy and at the same time is highly correlated with the carrier signal.

Embodiments of the invention may be implemented in any conventional computer programming language. For example, preferred embodiments may be implemented in a procedural programming language (e.g., "C") or an object oriented programming language (e.g., "C++", Python). Alternative embodiments of the invention may be implemented as preprogrammed hardware elements, other related signals, or as a combination of hardware and software signals.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of generating electrode stimulation signals for an implanted electrode array, the method comprising:
   processing an acoustic audio signal to generate a plurality of band pass signals, wherein each band pass signal includes a fine structure carrier signal and a modulator envelope signal;
   for each band pass signal:
   i. extracting fine time structure information from the carrier signal to determine a sequence of stimulation event signals,
   ii. for one or more low frequency band pass signals, sampling the modulator envelope signal synchronously with the carrier signal to create envelope weighted stimulation event signals,
   iii. for one or more higher frequency band pass signals,
      (1) if and only if the modulator envelope signal exceeds a sampling threshold value, then
      (2) sampling the modulator envelope signal synchronously with the carrier signal to create envelope weighted stimulation event signals,
   processing the envelope weighted stimulation event signals to produce electrode stimulation signals for the implanted electrode array.

2. A method according to claim 1, wherein processing the envelope weighted stimulation event signals includes mapping the envelope weighted stimulation event signals to a set of electrode stimulation channels for producing the electrode stimulation signals.

3. A method according to claim 1, wherein processing the envelope weighted stimulation signals includes optimizing the envelope weighted stimulation signals for perception by the individual patient.

4. A method according to claim 1, wherein processing the envelope weighted stimulation event signals includes developing a desired pulse shape for the electrode stimulation signals.

5. A method according to claim 4, wherein the desired pulse shape is a biphasic pulse.

6. A method according to claim 1, wherein extracting fine time structure information is based on zero crossings of the band pass signals.

7. A method according to claim 1, further comprising:
   for each band pass signal, suppressing the envelope weighted stimulation signals if one or more physiological state considerations occur.

8. A method according to claim 7, wherein the one or more physiological state considerations includes a refractory state of target nervous tissue.

9. A method according to claim 7, wherein the one or more physiological state considerations includes adjacent channel stimulation activity.

10. A method according to claim 1, wherein the sampling threshold value is a function of channel signal quality.

11. A method according to claim 1, wherein the sampling threshold value is a function of one or more physiological criteria.

12. A method according to claim 1, wherein the sampling threshold value is a function of one or more temporal characteristics of the modulator envelope signal.

13. A cochlear implant system adapted to use the method according to any of claims 1-12.

14. A computer program product implemented in a non-transitory computer readable storage medium for generating electrode stimulation signals for an implanted electrode array, the product comprising:
program code for processing an acoustic audio signal to generate a plurality of band pass signals, wherein each band pass signal includes a fine structure carrier signal and a modulator envelope signal;
program code for each band pass signal for:
  i. extracting fine time structure information from the carrier signal to determine a sequence of stimulation event signals,
  ii. for one or more low frequency band pass signals, sampling the modulator envelope signal synchronously with the carrier signal to create envelope weighted stimulation event signals,
  iii. for one or more higher frequency band pass signals,
    (1) if and only if the modulator envelope signal exceeds a sampling threshold value, then
    (2) sampling the modulator envelope signal synchronously with the carrier signal to create envelope weighted stimulation event signals,
program code for processing the envelope weighted stimulation event signals to produce electrode stimulation signals for the implanted electrode array.

15. A product according to claim 14, wherein the program code for processing the envelope weighted stimulation event signals includes program code for mapping the envelope weighted stimulation event signals to a set of electrode stimulation channels for producing the electrode stimulation signals.

16. A product according to claim 14, wherein the program code for processing the envelope weighted stimulation signals includes program code for optimizing the envelope weighted stimulation signals for perception by the individual patient.

17. A product according to claim 14, wherein the program code for processing the envelope weighted stimulation event signals includes program code for developing a desired pulse shape for the electrode stimulation signals.

18. A product according to claim 17, wherein the desired pulse shape is a biphasic pulse.

19. A product according to claim 14, wherein extracting fine time structure information is based on zero crossings of the band pass signals.

20. A product according to claim 14, further comprising:
program code for each band pass signal for suppressing the envelope weighted stimulation signals if one or more physiological state considerations occur.

21. A product according to claim 20, wherein the one or more physiological state considerations includes a refractory state of target nervous tissue.

22. A product according to claim 20, wherein the one or more physiological state considerations includes adjacent channel stimulation activity.

23. A product according to claim 14, wherein the sampling threshold value is a function of channel signal quality.

24. A product according to claim 14, wherein the sampling threshold value is a function of one or more physiological criteria.

25. A product according to claim 14, wherein the sampling threshold value is a function of one or more temporal characteristics of the modulator envelope signal.

* * * * *